(12) United States Patent
Sardashti et al.

(10) Patent No.: US 7,782,448 B2
(45) Date of Patent: Aug. 24, 2010

(54) ANALYSIS OF THE EFFECTS OF A FIRST SUBSTANCE ON THE BEHAVIOR OF A SECOND SUBSTANCE USING SURFACE ENHANCED RAMAN SPECTROSCOPY

(75) Inventors: Maziar Sardashti, Bartlesville, OK (US); Frank J. McEnroe, Ponca City, OK (US); David J. Blumer, Bartlesville, OK (US)

(73) Assignee: ConocoPhillips Company, Houston, TX (US)

( * ) Notice: Subject to any disclaimer, the term of this patent is extended or adjusted under 35 U.S.C. 154(b) by 244 days.

(21) Appl. No.: 12/116,415

(22) Filed: May 7, 2008

(65) Prior Publication Data

US 2009/0279073 A1    Nov. 12, 2009

(51) Int. Cl.
*G01J 3/44* (2006.01)
*G01N 21/65* (2006.01)

(52) U.S. Cl. .......................................... 356/72; 356/301
(58) Field of Classification Search .................... 356/72, 356/301
See application file for complete search history.

(56) References Cited

U.S. PATENT DOCUMENTS 6,954,560 B2    10/2005   Tolmachev et al.

6,989,897 B2    1/2006   Chan et al.

FOREIGN PATENT DOCUMENTS

WO    WO 2004/008091 A1    1/2004

OTHER PUBLICATIONS

Kester et al., Surface Enhanced Raman Scattering in Corrosion Science: Benzotriazole on Copper, J. Electrochem. Soc.: Electrochemical Science and Technology, vol. 129, No. 8, Aug. 1982, pp. 1716-1719.*
Thierry et al., Simultaneous Raman Spectroscopy and Electrochemical Studies of Corrosion Inhibiting Molecules on Coppper, J. Electrochem. Soc.: Electrochemical Science and Technology, vol. 132, No. 5, May 1985, pp. 1009-1014.*
Bernard et al., In situ Raman Study of the Corrosion of Zinc-Coated Steel in the Presence of Chloride, J. Electrochem. Soc., vol. 142, No. 7, Jul. 1995, pp. 2167-2170.*

* cited by examiner

*Primary Examiner*—F. L Evans (57) ABSTRACT

A method of analyzing an effect of a first substance on the behavior of a second substance comprises exposing a test material to the first substance, performing a first surface enhanced Raman spectroscopy analysis of the test material while it is exposed to the first substance, exposing the test material to the first substance and to the second substance, and performing a second surface enhanced Raman spectroscopy analysis of the test material while it is exposed to the first substance and to the second substance. Results of the first and second analyses are compared to identify a change in the behavior of the first substance.

25 Claims, 8 Drawing Sheets

(12) United States Patent
US 7,782,448 B2

ANALYSIS OF THE EFFECTS OF A FIRST SUBSTANCE ON THE BEHAVIOR OF A SECOND SUBSTANCE USING SURFACE ENHANCED RAMAN SPECTROSCOPY

BACKGROUND

1. Field

The present technology relates to a method of spectroscopy analysis. More particularly, embodiments of the technology involve a system and method for performing surface enhanced Raman spectroscopy to determine the effect of the presence of a first substance on the behavior of a second substance in a test fluid.

2. Related Art

Petroleum production involves substances, such as brine, that can be damaging to production, transportation, and/or processing equipment. Thus, in petroleum production it is often desirable to combine an additive, such as a corrosion inhibitor, with the petroleum product, such as oil, to preserve the product and/or equipment during the production, transportation, and/or processing processes. Such additives may be tested in a laboratory setting to determine their effectiveness. Often, multiple additives are added to oil or other petroleum products to simultaneously address multiple different problems. Conventional testing methods fail to adequately determine the effectiveness of using multiple additives simultaneously.

Thus, there is a need for an improved process for analyzing the effectiveness of petroleum additives that does not suffer from the limitations of conventional testing processes.

SUMMARY

According to a first embodiment of the invention, a method of analyzing an effect of a first substance on the behavior of a second substance comprises exposing a test material to the first substance; performing a first surface enhanced Raman spectroscopy analysis of the test material while it is exposed to the first substance; exposing the test material simultaneously to the first substance and to the second substance; performing a second surface enhanced Raman spectroscopy analysis of the test material while it is exposed to the first substance and to the second substance; and comparing a result of the first analysis with a result of the second analysis and identifying a change in the behavior of the first substance based on a difference between the first result and the second result.

According to a second embodiment of the invention, a method of analyzing an effect of a first substance on the behavior of a second substance comprises exposing a test material to the first substance; applying an electric potential to the test material while it is exposed to the first substance, varying the electric potential, measuring a first current through the test material as the electric potential is varied, and performing a first surface enhanced Raman spectroscopy analysis of the test material while it is exposed to the first substance by collecting a plurality of SERS spectra each at a different electric potential; exposing the test material to the first substance and to the second substance; applying an electric potential to the test material while it is exposed to the first substance and to the second substance, varying the electric potential, measuring a second current through the test material as the electric potential is varied, and performing a second surface enhanced Raman spectroscopy analysis of the test material while it is exposed to the first substance by collecting a plurality of SERS spectra each at a different electric potential; and comparing the first current with the second current, comparing a result of the first analysis with a result of the second analysis, and identifying a change in the behavior of the first substance based on differences between the result of the first analysis and the result of the second analysis and between the first current and the second current.

According to a third embodiment of the invention, a method of determining an effect of a first petroleum additive on the performance of a second petroleum additive comprises (a) placing a test fluid within a test chamber of a test cell, wherein the test fluid simulates an actual fluid present during a petroleum production operation and includes a first petroleum additive, wherein the test chamber is at least partially enclosed by a wall, and wherein the wall includes a window; (b) placing a test material within the test chamber, wherein at least a portion of the test material is in contact with the test fluid, and wherein at least a portion of the test material is in optical register with the window; (c) placing a first conductive element in electrical communication with the test fluid such that the first conductive element is separated from the test material by a space and extends to an outside of the cell; (d) placing a second conductive element in electrical communication with the test material such that the second conductive element extends to the outside of the cell; (e) applying an electric potential to the test material using the first conductive element and the second conductive element; (f) performing a first spectroscopy analysis on the test material by exposing the test material to light generated by a spectroscopy emitter and capturing light reflected from the test material using a spectroscopy sensor; (g) adding a second additive to the test solution; (h) repeating steps (c), (d), and (e); (i) performing a second spectroscopy analysis on the test material by exposing the test material to light generated by a spectroscopy emitter and capturing light reflected from the test material using a spectroscopy sensor; and (j) comparing results of the first spectroscopy analysis and the second spectroscopy analysis to identify an effect of the second additive on a behavior of the first additive.

BRIEF DESCRIPTION OF THE DRAWING FIGURES

A preferred embodiment of the present technology is described in detail below with reference to the attached drawing figures, wherein.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of embodiments of the present invention references the accompanying drawings that illustrate specific embodiments in which the invention may be practiced. The embodiments are intended to describe aspects of the technology in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

Embodiments of the present invention can be carried out using a test cell similar to the one illustrated in FIGS. 1-6, which is designated generally by the reference numeral 10. The cell 10 may be used in spectroscopy analyses, including SERS, and generally includes a cell body 12 with a window 14, a first electrode tube 16, a second electrode tube 18, and a third electrode tube 20.

The body 12 may be cylindrical in shape (as illustrated), comprising a circular bottom wall 22, an annular side wall 24, and a circular top wall 26. The top wall 26 presents a recessed portion 28 that includes the window 14. The bottom wall 22, side wall 24, and top wall 26 may form a single, integral wall that defines an internal test chamber 30 that is adapted to hold a test fluid 32, explained below in greater detail. The walls 22,24,26 may be constructed of substantially any suitably durable material including glass, plastic, metal, or the like. Constructing the walls 22,24,26 of a substantially transparent material may be desirable to enable a user to view the contents of the cell 10 from various angles. In a particular embodiment, the walls 22,24,26 are constructed of PYREX.

While the body 12 is illustrated and described as being generally cylindrical in shape, embodiments of the invention may present other, equally-preferred shapes without departing from the spirit or scope of the present teachings. By way of example, the body 12 may present a rectangular, ovular, or arbitrary shape.

The recessed portion 28 is a generally planar region of the top wall 26 surrounding and including the window 14. While the recessed portion 28 is illustrated as presenting a circular pattern, the present teachings are not so limited and the recessed portion 28 may present other, equally-preferred patterns including, for example, rectangular patterns or arbitrarily-shaped patterns. The recessed portion 28 is generally parallel with the non-recessed portion of the top wall 26, though offset by a distance within the range of from about 0.5 mm to about 3.5 mm or within the range of from about 1.0 mm to about 3.0 mm. More particularly, the recessed portion 28 may be offset from the non-recessed portion of the top wall 26 a distance of about 1.5 mm, about 2.0 mm, or about 2.5 mm. The recessed portion 28 may be useful, for example, to facilitate spectroscopy analysis by accommodating placement of an optical component proximate the window 14.

The window 14 is a region that allows light to pass through with minimal scattering, and thus is transparent or substantially transparent. The window may be an uncovered aperture in the top wall 26, or may include a thin plate or sheet of transparent material separating the test chamber 30 from outside the cell 10. By way of example, the window 14 may include a hole in the top wall 26 and a thin sheet of transparent material 34, such as a thin sheet of glass or plastic similar to a microscope slide cover, secured to a top or outer surface of the top wall 26. The thin sheet of transparent material 34 may be separate from the top wall 26 and secured thereto using an adhesive, such as a resin. Alternatively, the thin sheet of transparent material 34 may be an integral part of the top wall 26. The sheet of transparent material 34 may be substantially thinner than the wall 26, as explained below in greater detail.

The window 14 may be circular (as illustrated) and may have a diameter within the range of from about 0.5 cm to about 2.5 cm or within the range of from about 1.0 cm to about 2.0 cm. More particularly, the diameter of the window 14 may be about 1.3 cm, about 1.5 cm, or about 1.7 cm. The window 14 need not be circular but may present other shapes, including, for example, rectangular and triangular shapes. Regardless of the particular shape of the window 14, it may present an area within the range of from about 0.10 $cm^2$ to about 5.0 $cm^2$ or within the range of from about 1.0 $cm^2$ to about 4.0 $cm^2$. More particularly, the are of the window may be about 1.5 $cm^2$, about 2.0 $cm^2$, about 2.5 $cm^2$, about 3.0 $cm^2$, or about 3.5 $cm^2$.

The bottom wall 22, side wall 24, and top wall 26 may each present a thickness within the range of from about 0.3 mm to about 1.7 mm, within the range of from about 0.5 mm to about 1.5 mm, or within the range of from about 0.7 mm to about 1.3 mm. More particularly, the bottom wall 22, side wall 24, and top wall 26 may each present a thickness of about 0.9 mm, about 11.0 mm, or about 1.1 mm. The window 14 may present a thickness within the range of from about 0.1 mm to about 0.3 mm or from about 0.15 mm to about 0.25 mm. More particularly, the window 14 may be about 0.17 mm thick, about 0.20 mm thick, or about 0.23 mm thick.

A diameter of the annular side wall 24 may be within the range of from about 2.0 cm to about 10.0 cm, within the range of from about 4.0 cm to about 8.0 cm, or within the range of from about 5.0 cm to about 7.0 cm. More particularly, the diameter of the annular wall 24 may be about 5.7 cm, about 6.0 cm, or about 6.3 cm. A volume of the test chamber 30 may be within the range of from about 20 $cm^3$ to about 60 $cm^3$ or from about 30 $cm^3$ to about 50 $cm^3$. More particularly, the volume of the test chamber 30 may be about 35 $cm^3$, about 40 $cm^3$, or about 45 $cm^3$.

The first electrode tube 16 houses a reference electrode including a conductive element 36 and a reference fluid 38. An outer tubular wall 40 and an end cap 42 of the tube 16 define an internal chamber that retains the reference fluid 38. A salt bridge 44 separates the reference fluid 38 from the test fluid 32 in the test chamber 30.

The reference fluid 38 provides a known electrochemical potential used as a base or background potential when, for example, applying an electric potential to a test material within the cell 10. The reference fluid 38 may be a salt solution that includes, for example, silver chloride, potassium chloride, or silver nitrate. The salt bridge 44 provides a physical barrier between the reference fluid 38 of the tube 16 and the test fluid 32 of the internal test chamber 30 while allowing electron migration between the reference fluid 38 and the test fluid 32. The salt bridge 44 may include the same salt that is used in the reference fluid 38. The reference fluid 38 and the salt bridge 44 may be conventional in nature.

The conductive element 36 may be silver or platinum wire or foil extending from a location within the tube 16 proximate the salt bridge 44 through the end cap 42 to provide means for placing an external apparatus, such as a potentiostat, in electrical communication with the reference fluid 38. Thus, the conductive element 36 is in electrical communication with the reference fluid 38 but does not contact the salt bridge 44.

A first end of the electrode tube 16 attaches to or is integral with the cell body 12 and a second end of the electrode tube 16 (including the end cap 42) extends generally upwardly and outwardly from the cell body 12. A diameter of the tube 16 may be within the range of from about 0.5 cm to about 1.5 cm or within the range of from about 0.7 cm to about 1.3 cm. More particularly, the diameter of the tube 16 may be about 0.85 cm, about 0.90 cm, or about 0.95 cm. A length of the tube 16 may be within the range of from about 1.0 cm to about 5.0 cm or within the range of from about 2.0 cm to about 4.0 cm. More particularly, the length of the tube 16 may be about 2.5 cm, about 3.0 cm, or about 3.5 cm.

The second electrode tube 18 is defined by a tubular wall 46 that houses a working electrode 48 including, for example, a wire 50 encapsulated in electrically insulating material 52 extending from an outside of the tube 18, through an end cap 54, to a test material 56. The test material 56 may be a specimen of any material that is the target of the analysis or test and may be, for example, a piece of metal of the kind used in a pipeline or a holding tank. The test material 56 is electrically and physically connected to the wire 50 such that the test material 56 may be inserted into the test chamber 30 by inserting the material 56 and the wire 50 through a mouth of the second electrode tube 18.

A first end of the electrode tube 18 attaches to or is integral with the cell body 12 and a second end of the electrode tube 18 extends generally upwardly and outwardly from the cell body 12. A diameter of the tube 18 may be within the range of from about 0.5 cm to about 2.0 cm or within the range of from about 1.0 cm to about 1.5 cm. More particularly, the diameter of the tube 18 may be about 1.2 cm, about 1.3 cm, or about 1.4 cm. A length of the tube 18 may be within the range of from about 1.0 cm to about 5.0 cm or within the range of from about 2.0 cm to about 4.0 cm. More particularly, the length of the tube 18 may be about 2.5 cm, about 3.0 cm, or about 3.5 cm.

The test material 56 is preferably planar and may present substantially any shape, including, for example, a rectangular or circular shape. If the material 56 is rectangular, a length and a width of the material 56 may each be within the range of from about 1.0 mm to about 15.0 mm or within the range of from about 2.0 mm to about 14.0 mm. More particularly, the length and the width of the material 56 may each be about 9.5 mm, about 10.0 mm, or about 10.5 mm. A depth or thickness of the material 56 may be within the range of from about 0.5 mm to about 5.0 mm or within the range of from about 0.6 mm to about 4.5 mm. More particularly, the thickness of the material 56 may be about 2.5 mm, about 3.0 mm, or about 3.5 mm.

The third electrode tube 20 houses a counter electrode including a conductive element 58. An outer tubular wall 60 of the tube 20 holds an electrically insulating retaining material 62. The retaining material 62 includes an axial through-hole that receives and supports the conductive element 58. The conductive element 58 may include a platinum wire that extends from an outside of the tube 20 into the test chamber 30 and in contact with the test fluid 32.

A diameter of the tube 20 may be within the range of from about 0.5 cm to about 1.5 cm or within the range of from about 0.7 cm to about 1.3 cm. More particularly, the diameter of the tube 14 may be about 0.85 cm, about 0.90 cm, or about 0.95 cm. A length of the tube 16 may be within the range of from about 1.0 cm to about 5.0 cm or within the range of from about 2.0 cm to about 4.0 cm. More particularly, the length of the tube 16 may be about 2.5 cm, about 3.0 cm, or about 3.5 cm.

Portions of the test material 56 may be substantially entirely coated with an electrically and chemically insulating material such that only a face 64 of the test material 56 is exposed to, and in contact with, the test fluid 32. Thus, a face opposite the face 64, as well as various sides or edges, may be coated with the electrically insulating material. Exposing only the face 64 to the test fluid 32 facilitates determining with precision the total amount of surface area of the test material 56 exposed to the test fluid 32, which may be helpful or required in various spectroscopy analyses.

The first electrode tube 16 and the second electrode tube 18 may be radially separated by a first angle a, and the second electrode tube 18 and the third electrode tube 20 may be radially separated by a second angel b. The first angle a and the second angle b may each be within the range of from about 10° to about 170° or from about 30° to about 150°. More particularly, the first angle a and the second angle b may each be about 60°, about 70°, or about 80°. As explained above, each of the tubes 16,18,20 extends upwardly and outwardly relative to the body 12 of the cell 10. An upward angle c of each of the tubes 16,18,20 relative to the body 12 may be within the range of from about 10° to about 80° or within the range of from about 30° to about 70°. More particularly, the upward angle of each of the tubes 16,18,20 may be about 40°, about 45°, or about 50°.

The cell 10 may be used in spectroscopy analysis, such as surface enhanced Raman spectroscopy. A spectroscopy instrument 70 including a potentiostat 72 may be used with the cell 10 to perform the analyses as illustrated in the schematic diagram of FIG. 7. The potentiostat 72 is connected to the conductive elements 36, 50, and 58. An optical component 74, including a monochromatic light source 76, such as a laser, and an optical sensor 78, is positioned relative to the cell 10 to be generally in register with the window 14 so that light emitted from the light source 76 strikes the test material 56 and is reflected back toward the optical component 74 according to principles of spectroscopy.

Figures 1, 2:
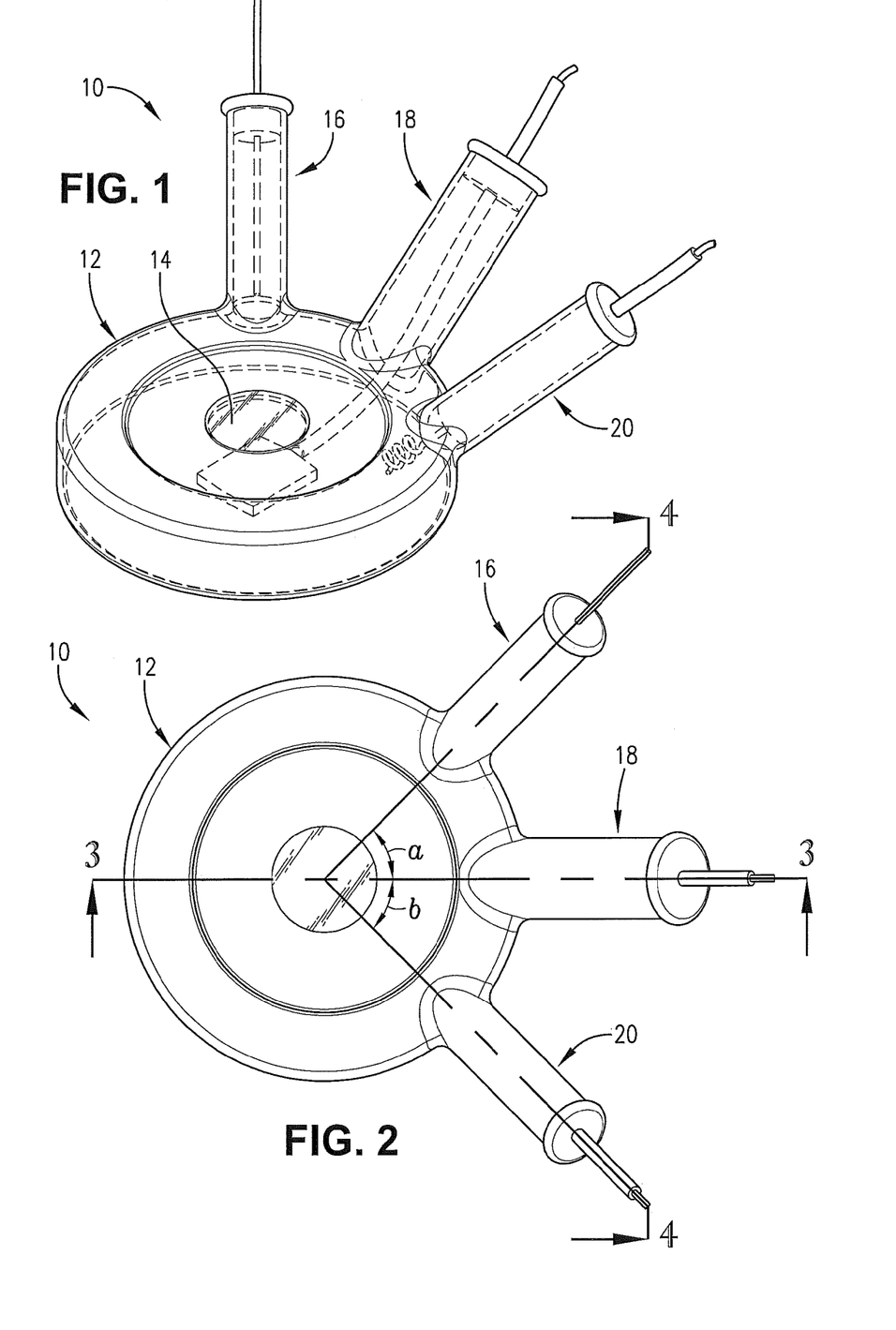
FIG. 1 is a perspective view of a test cell constructed according to principles of the present teachings and illustrating a test material placed within the cell.
FIG. 2 is a plan view of the cell of FIG. 1.
Figure 3:
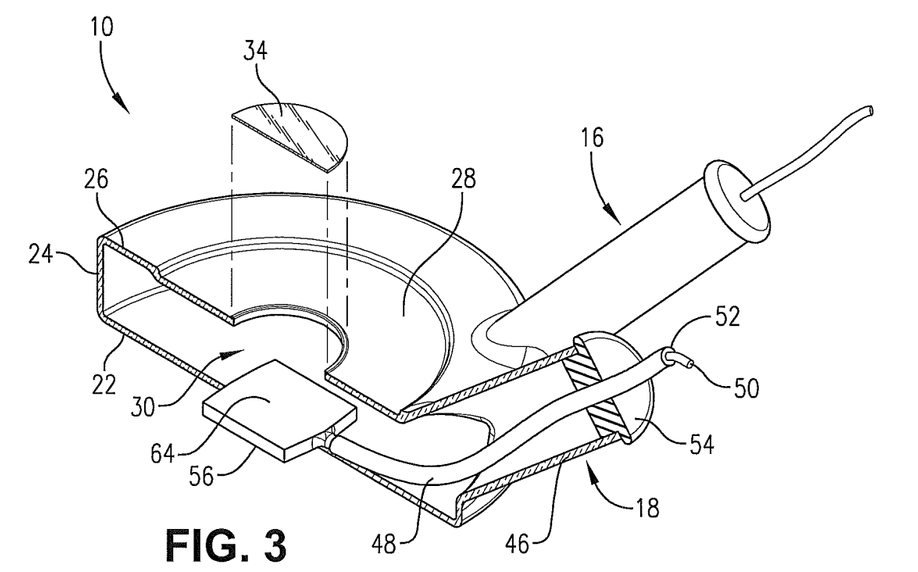
FIG. 3 is a cross-sectional view of the cell of FIG. 1 taken along line 3-3 of FIG. 2.
Figure 4:
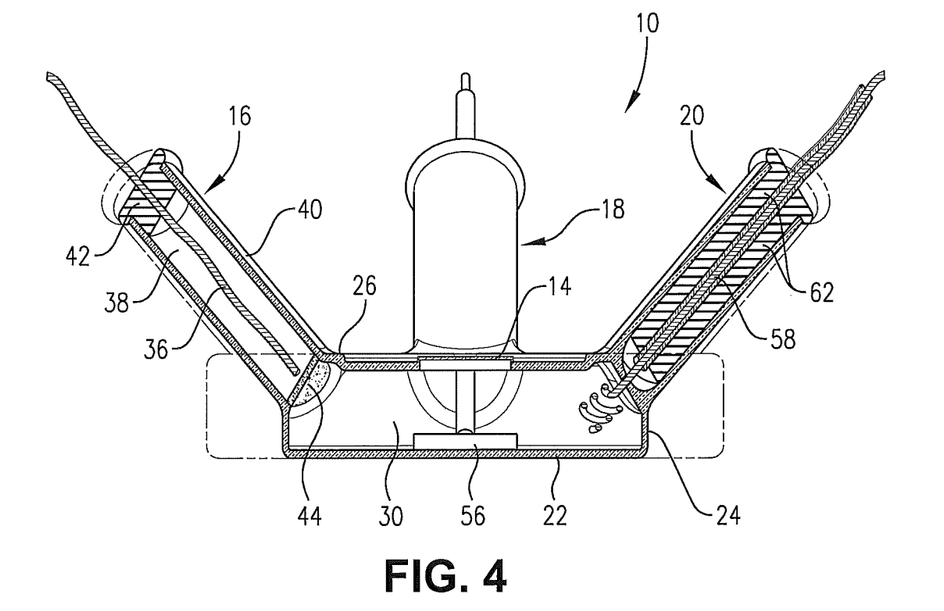
FIG. 4 is a cross-sectional view of the cell of FIG. 1 taken along line 4 of FIG. 2.
Figure 5:
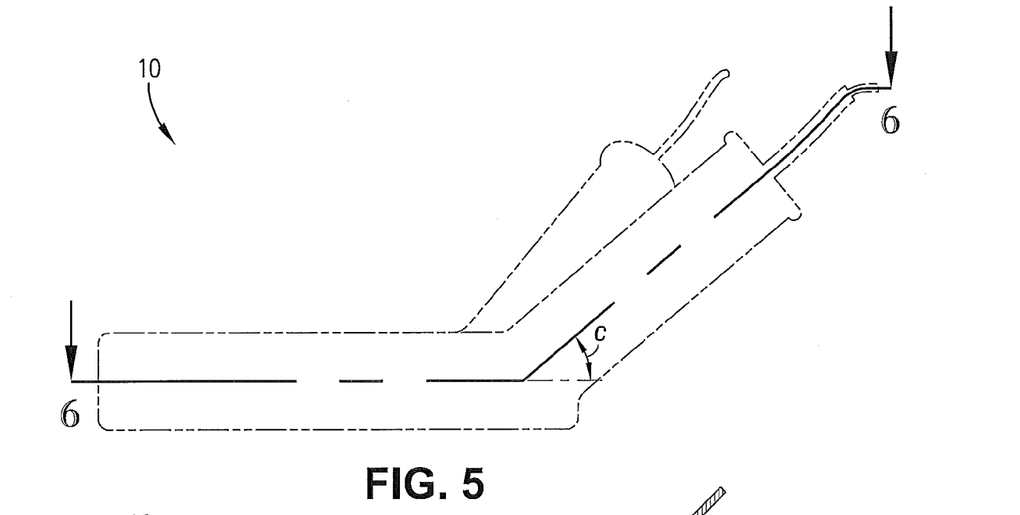
FIG. 5 is a side elevation view of the cell of FIG. 1 illustrating a perspective of FIG. 6.
Figure 6:
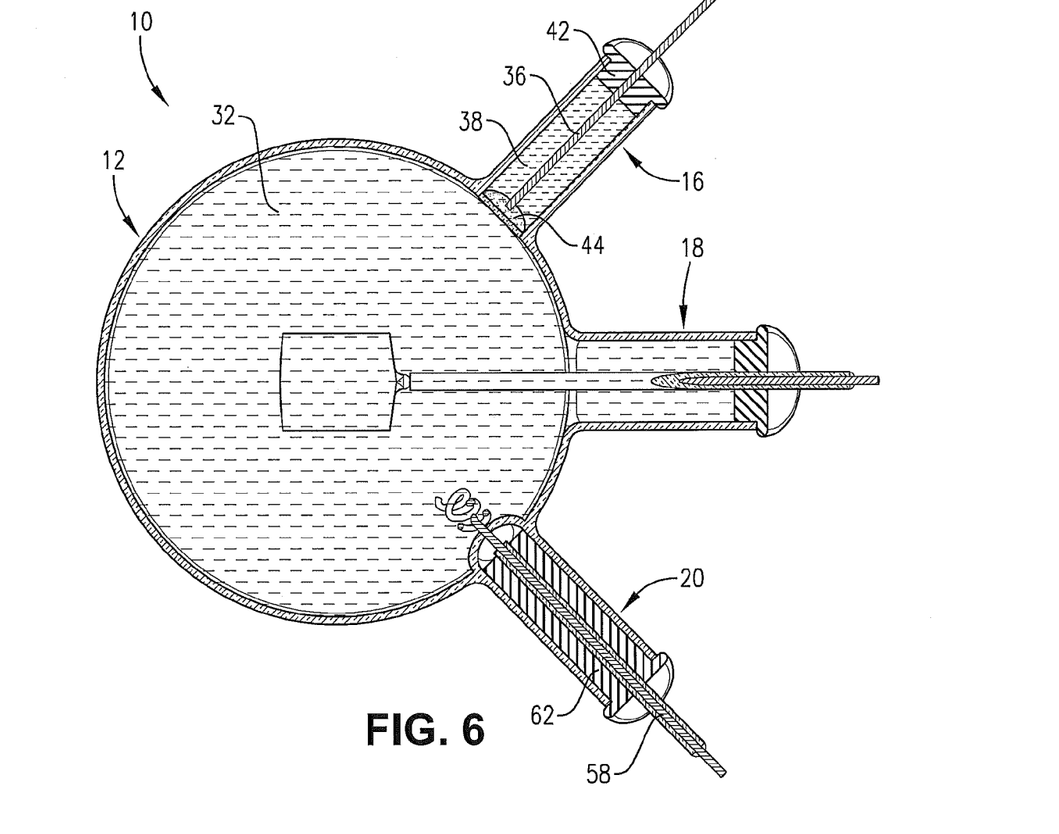
FIG. 6 is a cross-sectional view of the cell of FIG. 1 taken along line 6-6 of FIG. 5.
Figure 7:
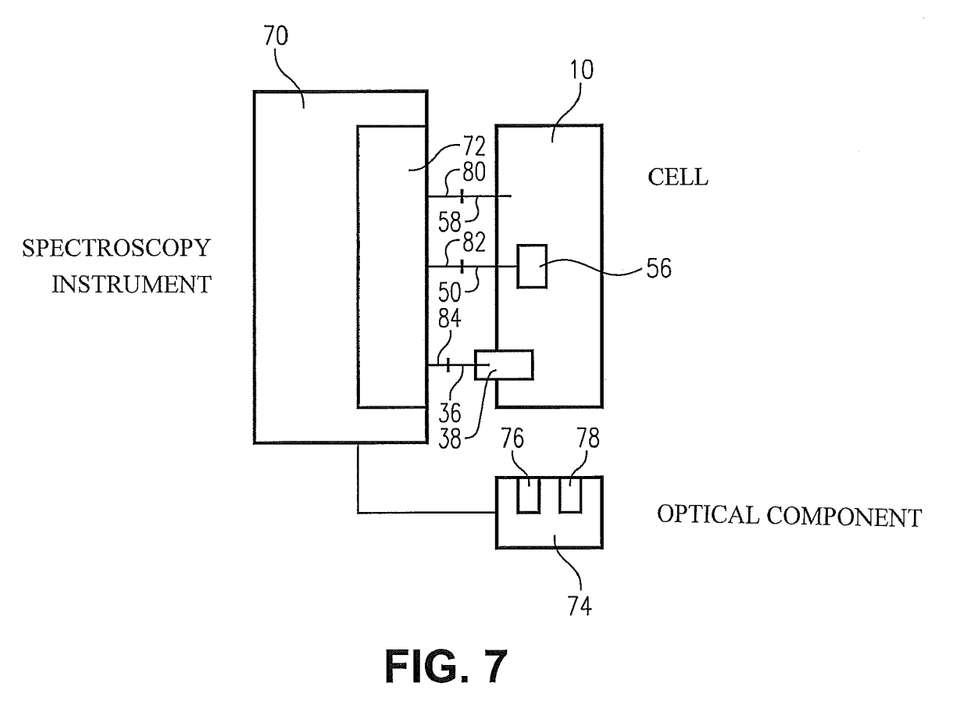
FIG. 7 is a schematic diagram of a spectroscopy system including the cell of FIG. 1 and a spectroscopy instrument.

The cell 10 is first positioned relative to the light source 76 so that light generated by the light source 76 is reflected by the test material 56 and focused on the light sensor 78. The step of positioning the light source 76 and the cell 10 relative to one another may take a few minutes. This presents a substantial advantage over the conventional methods of preparing a spectroscopy system which include manually moving emitters and sensors and could take hours to complete.

When the cell 10 is aligned with the optical component 74, the potentiostat 72 is electrically connected to the conductive elements 36,50,58. The instrument 70 measures the reference voltage on the conductive element 36 of the reference electrode and applies an electric potential to the test material 56 by applying an electric potential across the conductive element 50 of the working electrode and the conductive element 58 of the counter electrode. The precise voltage applied across the working and counter electrodes may vary from one application to another.

According to an exemplary application, an electric potential of 1200 mV is applied across the working and counter electrodes such that the working electrode is at approximately the same potential as the reference electrode, and a potential of −1200 mV is applied to the counter electrode relative to the working electrode. A SERS spectrum is captured at each of several pre-determined intervals by exposing the test material 56 to light generated by the light source 76, detecting the light reflected from the test material 56 with the optical sensor 78, and analyzing the light detected by the optical sensor 78 to gather information about the test material 56. By way of example, a new SERS spectrum may be captured every one-hundred seconds wherein the potential across the working and counter electrodes is increased by 1.0 mV/second until the potential across the conductive elements 50 and 58 is −300 mV.

The present technology can be used to generate SERS spectra using relatively low-power optics. For example, the light source 76 may be a laser emitter operable to generate laser light at a power of between 30 mW and 80 mW.

In various embodiments, the present invention involves a method of performing SERS analyses to identify the effect of the presence of a first substance on the behavior of a second substance in a test fluid. The method may be implemented in virtually any SERS test environment, such as the SERS cell 10 described above. Thus, while the method will be described as involving the SERS cell 10, it will be appreciated that the method is independent of any particular testing device.

By way of example, one situation in which it is desirable to determine the effect of the presence of a first substance on the behavior of a second substance is in petroleum production, where various additives may be used to preserve and/or protect equipment that is exposed to oil and other substances associated with petroleum production, transportation, and/or processing, such as brine. Thus, the exemplary method will be described with particular reference to chemicals and additives associated with oil production, transportation, and/or processing environments with the understanding that the present invention is not so limited and may be used for testing and analyzing virtually any substance that can be analyzed using SERS.

In various embodiments, the method involves exposing a piece of test material used in petroleum production, transportation, and/or processing to conditions simulating the actual in-the-field environment, introducing various substances, such as petroleum additives, into the environment, and performing SERS analyses to determine how the presence of one or more of the substances affects the behavior of one or more of the other substances.

The test material is first selected and prepared. The material may be a piece of metal, such as carbon steel, taken from a pipe or similar piece of equipment used in a petroleum production, transportation, and/or processing, and cut into a test piece of desired size. If the SERS cell 10 described above is used, for example, the test piece may be cut to approximately 1.0 cm wide, 1.0 cm long, and 0.25 cm thick.

The test material may be prepared via a process of polishing, cleaning and applying a SERS enhancing material. The test material may be polished using progressively finer polishing paper, such as, for example, 300 grit polishing paper followed by 600 grit polishing paper and then 1200 grit polishing paper. The cleaning may involve rinsing the test material with methanol or a similar cleaner for two to three minutes to remove organic material and contaminates that may not be removed by simply washing with water, and then rinsing the test material 56 with deionized water for another two to three minutes to remove the methanol. The water, methanol, or both may be applied using a sonicator. Additionally, one side of the test material may be drilled and tapped to attach a wire, such as the wire 50.

The test material 56 may be further cleaned by placing it in a degassed buffer solution (pH 6.8), and subjecting it to a negative electric potential for about thirty minutes using, for example, a potentiostat. The negative electric potential in this step cleans the surface of the test material 56 of any oxidation. This step may not be desirable with test material made of certain metals, such as gold.

The test material 56 may be partially coated with an electrically and/or chemically insulating material, as explained above. For example, portions of the test material 56 may be substantially entirely coated with an electrically and/or chemically insulating material such that only the face 64 of the test material 56 is exposed to, and in contact with, the test fluid 32. Exposing only the face 64 to the test fluid 32 facilitates determining with precision the total amount of surface area of the test material 56 exposed to the test fluid 32, which may be helpful or required in various steps of the spectroscopy analysis, such as, for example, the deposition of a SERS enhancer or measuring current density.

When the test material 56 has been polished and cleaned, a SERS enhancer may be applied to the test material. The SERS enhancer enhances a SERS signal derived from molecules attached to or located proximate the surface of the test material. In various embodiments, gold is applied to at least one surface of the test material to enhance the SERS effect. The gold or other SERS enhancer may be applied through an electrochemical deposition process.

According to an exemplary method of applying a gold SERS enhancer to the test material, the test material is first placed in a degassed solution of gold chloride where an electric potential is applied to the test material. The total charge may be monitored and is indicative of the amount of gold applied to the test material. The total charge may be within the range of from about 50 $mC/cm^2$ to about 150 $mC/cm^2$, or within the range of from about 70 $mC/cm^2$ to about 130 $mC/cm^2$. More particularly, the total charge applied to the test material may be about 80 $mC/cm^2$, about 90 $mC/cm^2$, about 100 $mC/cm^2$, about 110 $mC/cm^2$, or about 120 $mC/cm^2$. The gold does not entirely cover the test material, but rather covers a percentage of the material within the range of, for example, from about 1% to about 50%. More particularly, the percentage of gold or other SERS enhancing material covering the test material 56 surface may be about 5%, about 8%, about 10%, about 12%, or about 15%.

Figure 8:
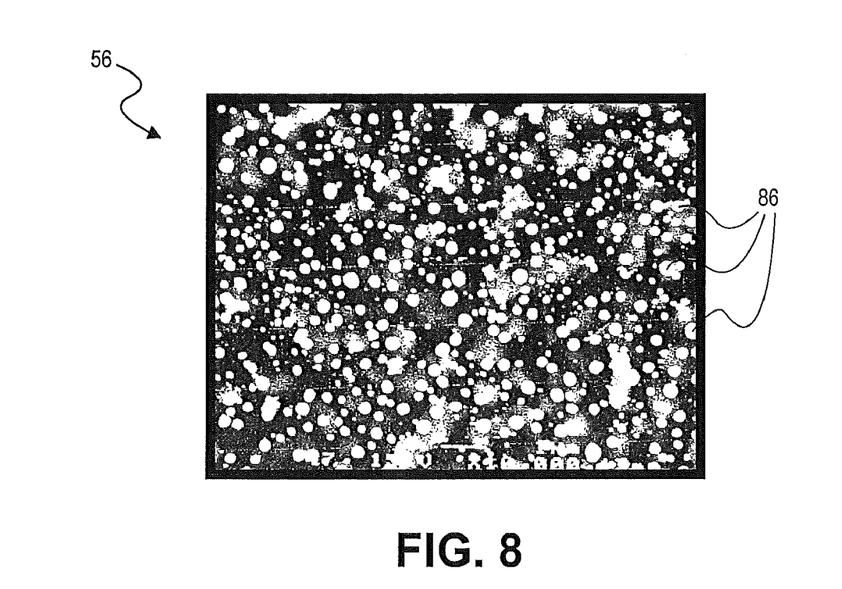
FIG. 8 illustrates a portion of a surface of the test material of FIG. 1 showing a SERS enhancer present on the surface.

An exemplary test material surface with a SERS enhancer deposited thereon is illustrated in FIG. 8. As can be seen from the drawing, the enhancer 86 is located in relatively isolated deposits that are approximately equally spaced throughout the surface.

Other exemplary materials that may be used as SERS enhancers include copper and silver. In some applications, however, the copper and silver may be less effective than gold as a SERS enhancer. Other metals may also be used, typically with less of an enhancing effect. Furthermore, as an alternative to adding a SERS enhancing material to the test material 56, the target surface of the test material 56 may be made rough to simulate the effect of the presence of a SERS enhancing material.

With the test material 56 thus prepared, it is ready to be placed in a test fluid, such as within the SERS cell 10 described above. The test fluid may simulate a fluid that is actually encountered in a particular working environment, such as a brine solution that is present in petroleum and contributes to deterioration of petroleum production, transportation, and/or processing equipment. When the actual fluid being simulated is brine, an exemplary synthetic brine recipe is as follows: 19.19 g of NaCl, 1.02 g of $CaCl_2.2H_2O$, 5.38 g of $MgCl_2.6H_2O$, 1.7 g of $Na_2SO_4$, and 0.28 g $NaHCO_3$ per liter of deionized water. This is but one example of a test fluid that may be used, and virtually any test fluid may be used according to the needs of a particular situation.

The test fluid may be maintained at a desired temperature and saturation. The temperature of the fluid may be regulated using a heating element external to the cell 10 and a temperature monitoring element, such as a thermocouple, that may be in contact with the test fluid via the electrode tube 18. An exemplary temperature is 55° C. The saturation of the test fluid (with, for example, $CO_2$ or $N_2$) may be regulating using a hose or similar device passed through the electrode tube 18. The hose may be connected to a gas cylinder regulator that generates a pressure of about 5 pounds per square inch of pressure. It may be desirable to saturate the test solution with $CO_2$ in order to, for example, simulate field conditions. Saturation of the test fluid with $CO_2$ may be accomplished, for example, by bubbling the $CO_2$ in the test fluid (within the SERS cell 10) for a period of thirty to forty-five minutes prior to performing the SERS tests.

Figure 9:
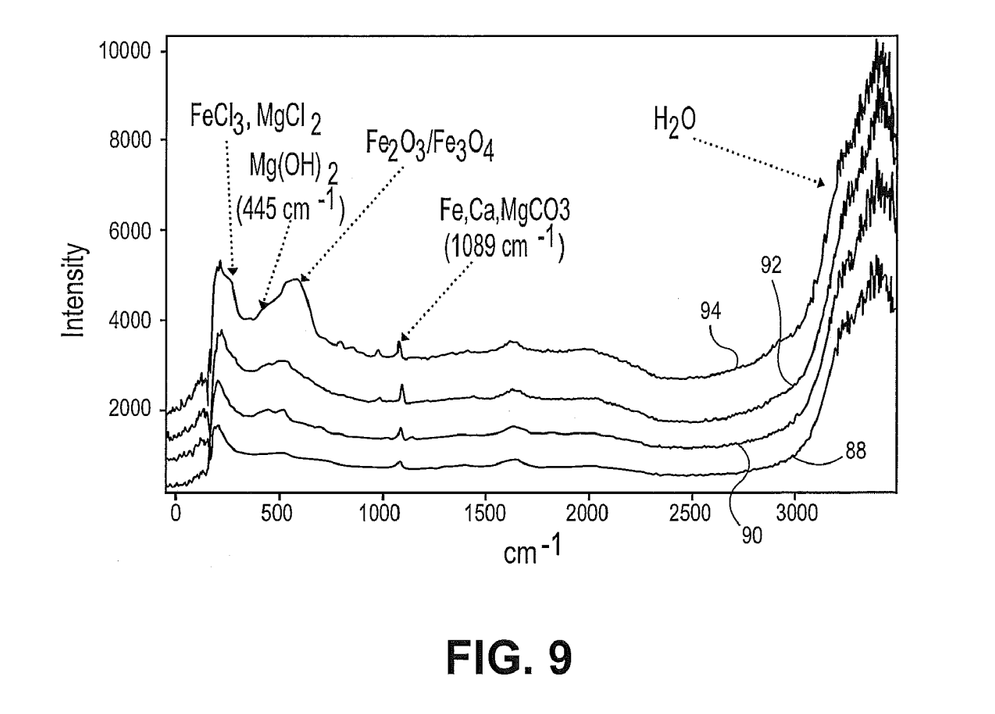
FIG. 9 is a graph illustrating the results of various SERS tests performed on the test material of FIG. 1 in the test cell of FIG. 1, wherein the test material is in the presence of a test fluid with no additives.

A SERS analysis is first performed on the test material 56 in the test fluid 32 but in the absence of any additives, wherein the test fluid 32 is placed in the SERS cell 10 along with the test material 56. A potential is applied to the test material 56 and gradually modified over time as SERS spectra are obtained at each of various potentials. A graph illustrating exemplary results of the test is depicted in FIG. 9, wherein a first line 88 represents a SERS spectra obtained at about −1240 mV, a second line 90 represents a SERS spectra obtained at about −960 mV, a third line 92 represents a SERS spectra obtained at about −680 mV, and a fourth line 94 represents a SERS spectra obtained at about −390 mV. Various peaks are attributed to the presence of certain substances near the surface of the test material 56, as indicated in the figure. SERS spectra obtained at more negative electric potentials generally reflect lower concentrations of the chemicals near the surface of the test material 56.

If the SERS cell 10 is used in the test illustrated in FIG. 9, the working electrode 50 and the counter electrode 58 are connected to a potentiostat, which is programmed to generate a potential of 1240 mV across the electrodes 50,58, with the electrode 50 being positive, and gradually decrease the potential as SERS spectra are obtained at predetermined time intervals.

A first additive is included in the solution and a second SERS analysis is performed to determine the performance of the first additive in the test solution. A corrosion inhibitor, for example, may be added to the test solution and tested to determine the performance of the corrosion inhibitor, such as the tendency to adhere to a surface of the test material 56. An exemplary corrosion inhibitor may include, for example, phosphate esters, such as phosphate monoester or a mixture of monoesters and diesters. To test the performance of the corrosion inhibitor, a SERS analysis may be performed on the test material in substantially the same manner as explained above, except that the corrosion inhibitor is present in the test fluid. Current through the test material 56 may also be monitored to determine the performance of the corrosion inhibitor, as explained below in greater detail.

Figure 10:
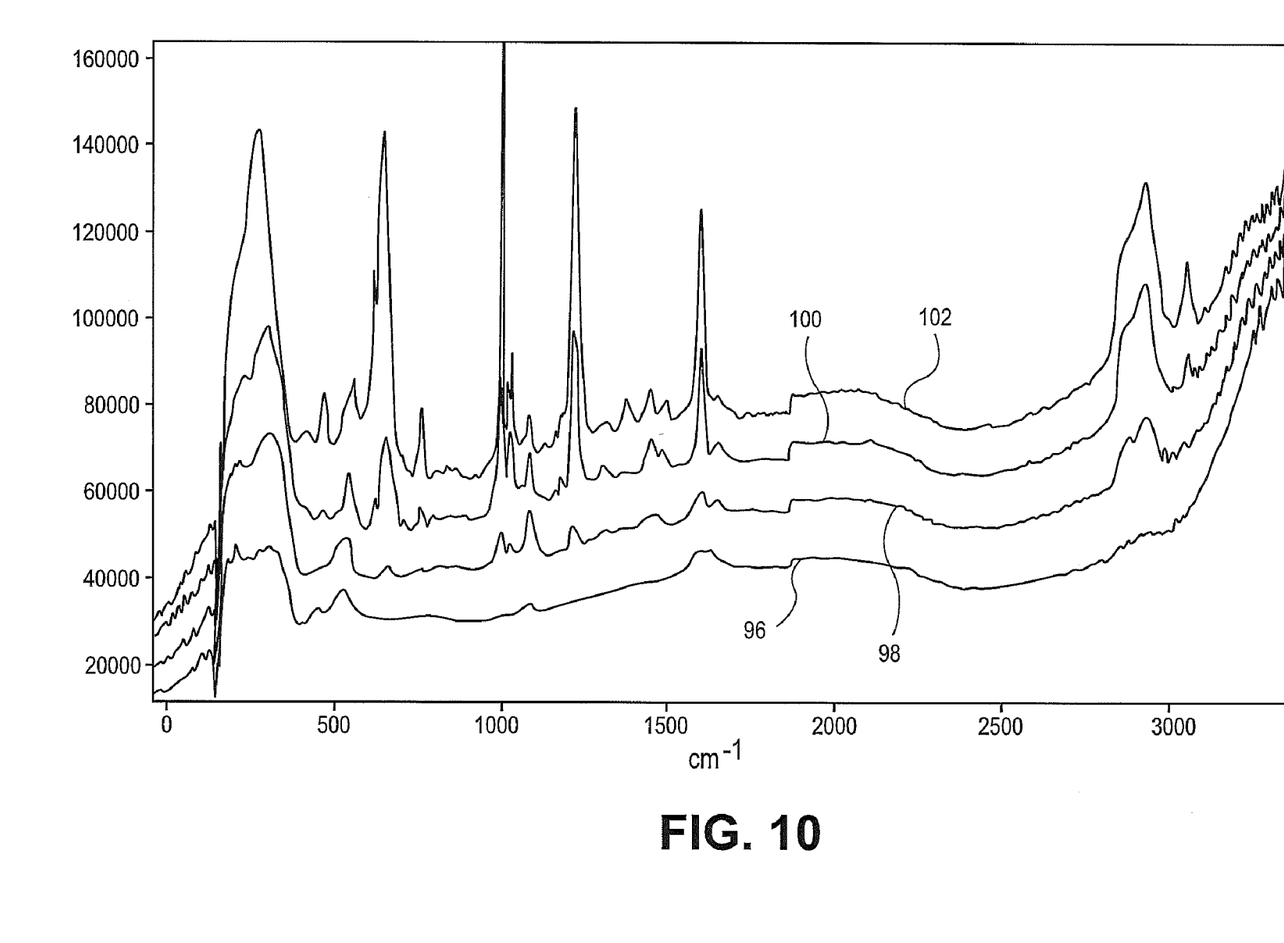
FIG. 10 is a graph illustrating the results of various SERS tests performed on the test material of FIG. 1 in the test cell of FIG. 1, wherein the test material is in the presence of a test fluid with a single additive.

An exemplary graph illustrating the results of a SERS analysis performed on the test material 56 is depicted in FIG. 10, wherein 100 ppm of a corrosion inhibitor have been added to the test solution (brine). The graph illustrated in FIG. 10 depicts a first SERS spectrum 96 obtained at −1240 mV, a second SERS spectrum obtained at −960 mV, a third SERS spectrum obtained at −660 mV, and a fourth SERS spectrum obtained at −370 mV. The SERS signals due to the corrosion inhibitor are very low under more negative, reducing potentials (−1240 mV and −960 mV) and high for less negative, oxidizing potentials (−660 mV and −370 mV). This indicates that the corrosion inhibitor is attaching to the metal surface of the test material 56 as the surface is under corrosive conditions, which is what is expected from a good corrosion inhibitor. Most of the peaks in the spectra illustrated in FIG. 10 are due to quaternary amines present in the corrosion inhibitor. The larger peaks in the vicinity of 600-700, 980-1030, and 1200 $cm^{-1}$ are all due to an aromatic ring. The large peaks in the vicinity of 2800-2900 $cm^{-1}$ are due to the aliphatic CH stretch from the $CH_3$ and R groups. The small peak close to 3000 $cm^{-1}$ is assigned to the aromatic CH stretch.

Figure 11:
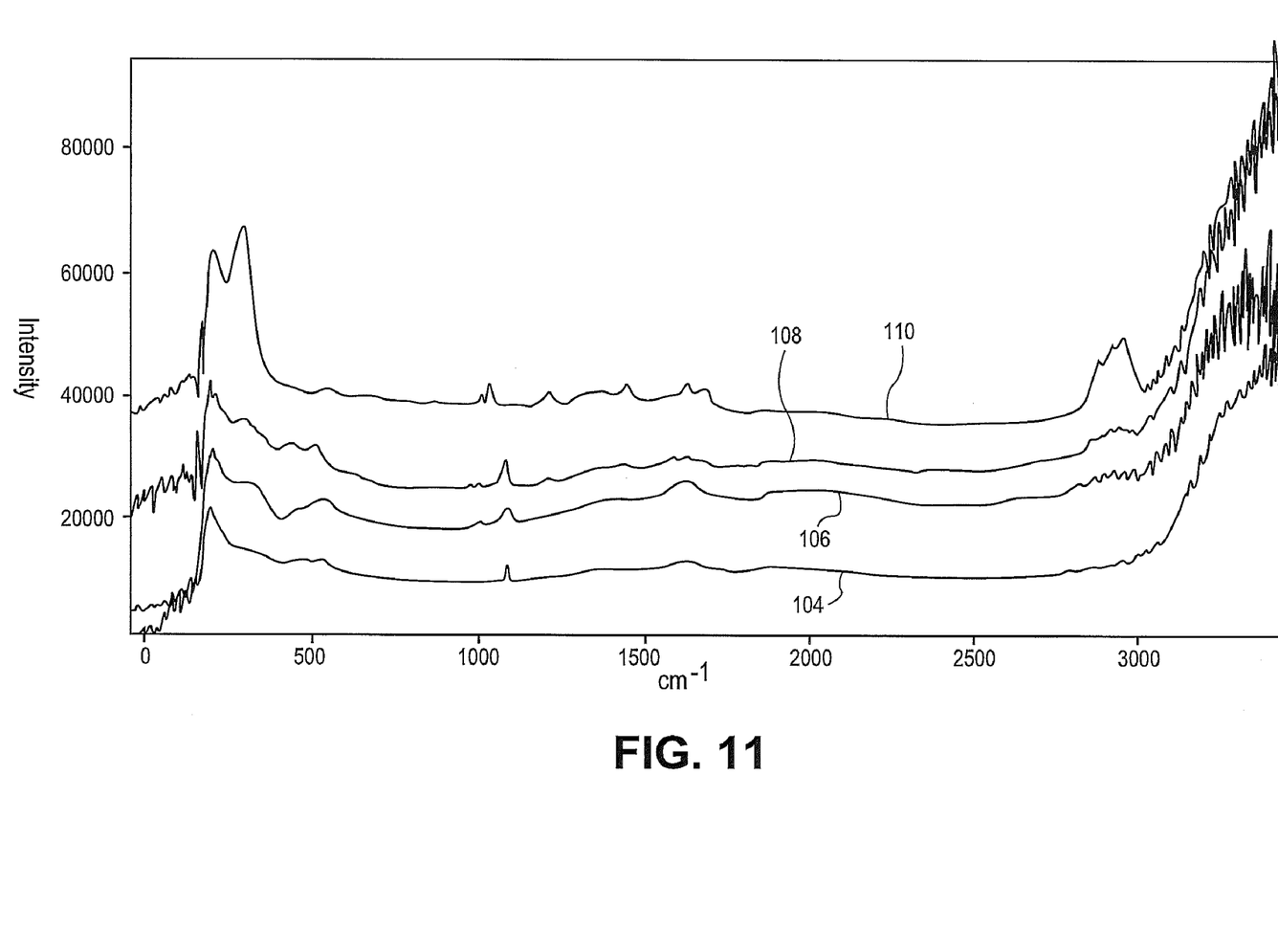
FIG. 11 is a graph illustrating the results of various SERS tests performed on the test material of FIG. 1 in the test cell of FIG. 1, wherein the test material is in the presence of a test fluid with two additives.

After the SERS analysis has been performed on the test solution with the first additive to determine the performance of the first additive in the absence of any other additives, the effects of one or more other additives on the performance of the first additive may be determined. Particularly, a SERS analysis may be performed on the test solution including the first additive and a second additive. By way of example, it may be desirable to determine the effect of a biocide, such as gluteraldehyde, on the performance of the corrosion inhibitor. To determine this, both the corrosion inhibitor and the biocide are added to the test solution and additional SERS analyses are run. The results of a test with both additives is illustrated in FIG. 11, which clearly indicates that the various elements are not present at the surface of the test material 56 in nearly the concentration as in FIG. 10, where the corrosion inhibitor was present without the biocide. Thus, the results of these two analyses illustrate the affect of the biocide on the performance of the corrosion inhibitor. In this case, the effect is undesirable as the biocide prevents the corrosion inhibitor from protecting the metal surface from corrosion.

While the process has generally been described using a corrosion inhibitor as the first additive and a biocide as the second additive to determine the effect of the biocide on the performance of the corrosion inhibitor, it will be appreciated that embodiments of the present invention may be used to determine the effect of the corrosion inhibitor on the performance of the biocide. Furthermore, other additives, such as scale inhibitors, emulsifiers, drilling additives, and hydrate inhibitors may be used as the first and/or second additive.

Figure 12:
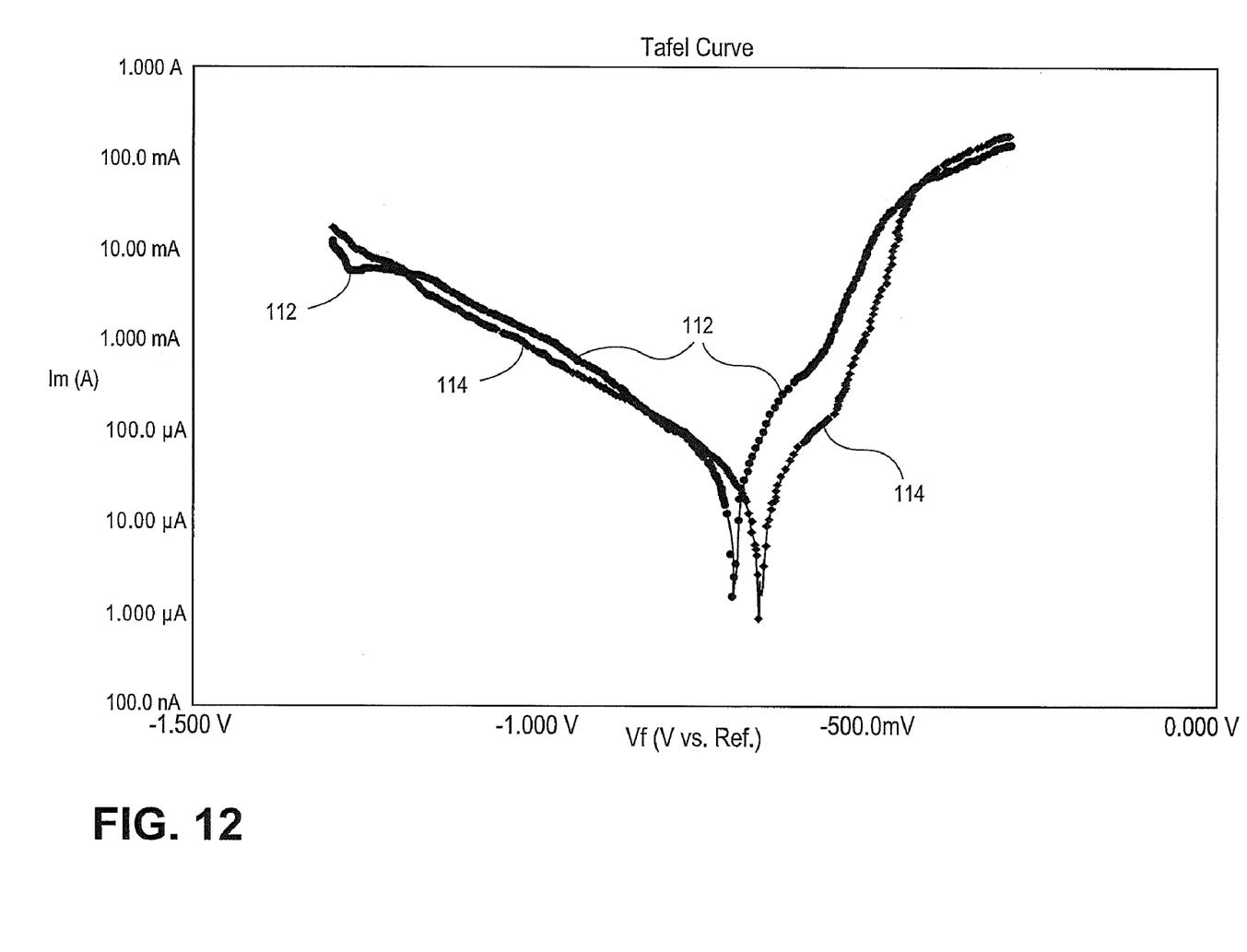
FIG. 12 is a graph illustrating a first Tafel curve taken from the test material in the presence of the test fluid and a single additive, and a second Tafel curve taken from the test material in the presence of the test fluid and two additives.

The performance of the corrosion inhibitor may further be determined by monitoring the current passing through the test material 56. A graph illustrating two plots of current density measurements is shown in FIG. 12. A first plot 112 illustrates current density over time through the test material 56 when both the corrosion inhibitor and the biocide are present in the test fluid 32. A second plot 114 illustrates current density over time through the test material 56 when only the corrosion inhibitor is present in the test fluid 32.

The point in the graph of FIG. 12 where each plot 112,114 is lowest is the corrosion potential, or the potential where corrosion begins to occur to the material 56. To the left of the corrosion potential is the reduction side where the material 56 is protected by ions on the surface of the material 56. To the right of the corrosion potential is the oxidation side of the curve, where corrosion may occur because the protective ions have moved away from the surface of the material 56. The plot 114 represents a more desirable performance of the corrosion inhibitor because, for example, the corrosion potential is lower (closer to zero volts) and the plot to the right of the corrosion potential is generally lower and presents a more gentle slope.

Although the invention has been described with reference to the embodiments illustrated in the attached drawing figures, it is noted that equivalents may be employed and substitutions made herein without departing from the scope of the invention as recited in the claims. For example, the particular form or function of the various attachment elements is not important to the present technology, and the attachment elements may present alternative shapes and sizes with equally-preferred results.

As used herein, the terms "a," "an," "the," and "said" means one or more.

As used herein, the terms "comprising," "comprises," and "comprise" are open-ended transition terms used to transition from a subject recited before the term to one or elements recited after the term, where the element or elements listed after the transition term are not necessarily the only elements that make up of the subject.

As used herein, the terms "containing," "contains," and "contain" have the same open-ended meaning as "comprising," "comprises," and "comprise," provided below.

As used herein, the terms "having," "has," and "have" have the same open-ended meaning as "comprising," "comprises," and "comprise," provided above As used herein, the terms "including," "includes," and "include" have the same open-ended meaning as "comprising," "comprises," and "comprise," provided above.

As used herein, a "conductor," "conductive element," or conductive material" is a material with an electrical resistivity of less than about $1\times10^{-3}$ $\Omega$m and more preferably less than about $1\times10^{-5}$ $\Omega$m.

As used herein, an "insulator," "insulating element," or "insulating material" is a material with an electrical resistivity of more than about 100 $\Omega$m and more preferably more than about $1\times10^3$ $\Omega$m.

Having thus described various embodiments of the invention, what is claimed as new and desired to be protected by Letters Patent includes the following:

1. A method of analyzing an effect of a first substance on the behavior of a second substance, said method comprising:
    exposing a test material to said first substance;
    performing a first surface enhanced Raman spectroscopy analysis of said test material while it is exposed to said first substance;
    exposing said test material simultaneously to said first substance and to said second substance;
    performing a second surface enhanced Raman spectroscopy analysis of said test material while it is exposed to said first substance and to said second substance; and
    comparing a result of said first analysis with a result of said second analysis and identifying a change in the behavior of said first substance based on a difference between said result of said first analysis and said result of said second analysis.

2. The method as set forth in claim 1, wherein said step of exposing a test material to said first substance involves creating a test fluid that simulates a fluid present in an actual environment, adding said first substance to said test fluid, and placing said test material at least partially in contact with said test fluid.

3. The method as set forth in claim 2, wherein said step of exposing said test material simultaneously to said first substance and to said second substance involves adding said second substance to said test fluid, and placing said test material at least partially in contact with said test fluid.

4. The method as set forth in claim 2, wherein creating a test fluid involves saturating said test fluid with a selected gas.

5. The method as set forth in claim 4, wherein said selected gas is chosen from the group consisting of $CO_2$ and $N_2$.

6. The method as set forth in claim 1, wherein said step of comparing a result of said first analysis with a result of said second analysis and identifying a change in the behavior of said first substance involves comparing SERS spectra.

7. The method as set forth in claim 1, further comprising:
    performing a third surface enhanced Raman spectroscopy analysis of said test material while it is exposed to said test fluid in the absence of said first substance and said second substance; and
    comparing a result of said third analysis with said result of said first analysis and identifying a behavior of said first substance based on a difference between said third result and said first result.

8. The method as set forth in claim 1, wherein said step of performing said first surface enhanced Raman spectroscopy analysis of said test material while it is exposed to said first substance involves applying an electric potential to said test material, varying said electric potential, and capturing a plurality of SERS spectra each at a different electric potential.

9. The method as set forth in claim 1, further comprising:
    applying an electric potential to said test material while it is exposed to said first substance only, varying said electric potential, and measuring a first current through said test material as said electric potential is varied;
    applying an electric potential to said test material while it is exposed to said first substance and to said second substance, varying said electric potential, and measuring a second current through said test material as said electric potential is varied; and
    comparing said first current density with said second current density and identifying a change in the behavior of said first substance based on a difference between said first current and said second current.

10. The method as set forth in claim 1, wherein said test material is carbon steel.

11. The method as set forth in claim 1, further comprising applying a SERS enhancer to at least a portion of a surface of said test material prior to performing said first surface enhanced Raman spectroscopy analysis, wherein said SERS enhancer is chosen from the group consisting of gold, silver and copper.

12. The method as set forth in claim 11, further comprising applying said SERS enhancer using an electrochemical deposition process.

13. The method as set forth in claim 1, further comprising:
    placing a test fluid within a test chamber of a test cell, wherein said test chamber is at least partially enclosed by a wall, and wherein said wall includes a window;
    placing said test material within said test chamber, wherein at least a portion of said test material is in contact with said test fluid, and wherein at least a portion of said test material is in optical register with said window;
    placing a first conductive element in electrical communication with said test fluid such that said first conductive element is separated from said test material by a space and extends to an outside of said cell;
    placing a second conductive element in electrical communication with said test material such that said second conductive element extends to said outside of said cell; and
    applying an electric potential to said test material using said first conductive element and said second conductive element.

14. The method as set forth in claim 13, further comprising heating said test fluid using a heating element external to said test cell.

15. The method as set forth in claim 1, wherein said first substance is chosen from the group consisting of a biocide, a scale inhibitor, and a corrosion inhibitor.

16. The method as set forth in claim 15, wherein said second substance is chosen from the group consisting of a biocide, a scale inhibitor, and a corrosion inhibitor.

17. The method as set forth in claim 1, wherein said test fluid includes brine.

18. A method of analyzing an effect of a first substance on the behavior of a second substance, said method comprising:
  exposing a test material to said first substance;
  applying an electric potential to said test material while it is exposed to said first substance, varying said electric potential, measuring a first current through said test material as said electric potential is varied, and performing a first surface enhanced Raman spectroscopy analysis of said test material while it is exposed to said first substance by collecting a plurality of SERS spectra each at a different electric potential;
  exposing said test material to said first substance and to said second substance;
  applying an electric potential to said test material while it is exposed to said first substance and to said second substance, varying said electric potential, measuring a second current through said test material as said electric potential is varied, and performing a second surface enhanced Raman spectroscopy analysis of said test material while it is exposed to said first substance by collecting a plurality of SERS spectra each at a different electric potential; and
  comparing said first current with said second current, comparing a result of said first analysis with a result of said second analysis, and identifying a change in the behavior of said first substance based on differences between said result of said first analysis and said result of said second analysis and between said first current and said second current.

19. The method as set forth in claim 18, further comprising applying a SERS enhancer to at least a portion of a surface said test material prior to performing said first surface enhanced Raman spectroscopy analysis.

20. The method as set forth in claim 19, further comprising applying said SERS enhancer using an electrochemical deposition process.

21. The method as set forth in claim 20, wherein said SERS enhancer is chosen from the group consisting of gold, silver and copper.

22. The method as set forth in claim 18, further comprising:
  placing a test fluid within a test chamber of a test cell, wherein said test chamber is at least partially enclosed by a wall, and wherein said wall includes a window;
  placing said test material within said test chamber, wherein at least a portion of said test material is in contact with said test fluid, and wherein at least a portion of said test material is in optical register with said window;
  placing a first conductive element in electrical communication with said test fluid such that said first conductive element is separated from said test material by a space and extends to an outside of said cell;
  placing a second conductive element in electrical communication with said test material such that said second conductive element extends to said outside of said cell; and
  applying said electric potential to said test material using said first conductive element and said second conductive element.

23. A method of determining an effect of a first petroleum additive on the performance of a second petroleum additive, said method comprising:
  (a) placing a test fluid within a test chamber of a test cell, wherein said test fluid simulates an actual fluid present during a petroleum production operation and includes a first petroleum additive, wherein said test chamber is at least partially enclosed by a wall, and wherein said wall includes a window;
  (b) placing a test material within said test chamber, wherein at least a portion of said test material is in contact with said test fluid, and wherein at least a portion of said test material is in optical register with said window;
  (c) placing a first conductive element in electrical communication with said test fluid such that said first conductive element is separated from said test material by a space and extends to an outside of said cell;
  (d) placing a second conductive element in electrical communication with said test material such that said second conductive element extends to said outside of said cell;
  (e) applying an electric potential to said test material using said first conductive element and said second conductive element;
  (f) performing a first spectroscopy analysis on said test material by exposing said test material to light generated by a spectroscopy emitter and capturing light reflected from said test material using a spectroscopy sensor;
  (g) adding a second additive to said test solution;
  (h) repeating steps (c), (d), and (e);
  (i) performing a second spectroscopy analysis on said test material by exposing said test material to light generated by a spectroscopy emitter and capturing light reflected from said test material using a spectroscopy sensor; and
  (j) comparing results of said first spectroscopy analysis and said second spectroscopy analysis to identify an effect of said second additive on a behavior of said first additive.

24. The method as set forth in claim 23, wherein said first additive is a biocide.

25. The method as set forth in claim 23, wherein said second additive is a corrosion inhibitor.

* * * * *